US005683717A

United States Patent [19]
Shen

[11] Patent Number: 5,683,717
[45] Date of Patent: Nov. 4, 1997

[54] GELATIN COATED MEDICAMENT AND PROCESS FOR MAKING SAME

[75] Inventor: Robert Wu-wei Shen, Kalamazoo, Mich.

[73] Assignees: Pharmacia & Upjohn Company, Kalamazoo; L. Perrigo Company, Allegan, both of Mich.

[21] Appl. No.: 349,693

[22] Filed: Dec. 2, 1994

Related U.S. Application Data

[63] Continuation of Ser. No. 169,956, Dec. 20, 1993, abandoned, which is a continuation of Ser. No. 992,640, Dec. 18, 1992, abandoned, which is a continuation of PCT/US91/03908, Jun. 28, 1990, which is a continuation of Ser. No. 545,943, Jun. 28, 1990, abandoned.

[51] Int. Cl.$^6$ ........................................ A61K 9/64
[52] U.S. Cl. ........................ 424/456; 424/460; 424/463; 424/474; 424/475
[58] Field of Search ........................... 424/456, 474, 424/476, 457

[56] References Cited

U.S. PATENT DOCUMENTS

| | | | |
|---|---|---|---|
| 4,820,524 | 4/1989 | Berta | 424/474 |
| 5,114,720 | 5/1992 | Littell et al. | 424/478 |
| 5,206,030 | 4/1993 | Wheatley et al. | 424/474 |

FOREIGN PATENT DOCUMENTS

| | | | |
|---|---|---|---|
| 0 279 682 A2 | 6/1988 | European Pat. Off. | A61J 3/00 |
| 0 319 318 A1 | 6/1989 | European Pat. Off. | A61J 3/06 |
| 65009992 | 5/1965 | Japan . | |
| 65009994 | 5/1965 | Japan . | |
| 74011044B | 10/1970 | Japan . | |
| 60084215 | 5/1985 | Japan . | |
| 930422 | 7/1963 | United Kingdom . | |

*Primary Examiner*—Thurman K. Page
*Assistant Examiner*—William E. Benston, Jr.
*Attorney, Agent, or Firm*—William G. Jameson

[57] ABSTRACT

This invention relates to coated medicaments and a process for providing spray coated gelatinous coverings for such medicaments. This invention is also directed to novel gelatinous compositions for spray coating tablets, caplets, pellets, granules and the like.

18 Claims, No Drawings

GELATIN COATED MEDICAMENT AND PROCESS FOR MAKING SAME

CROSS-REFERENCE TO RELATED APPLICATIONS

This application is a continuation of U.S. Ser. No. 08/169,956, filed 20 Dec. 1993 now abandoned which is a continuation of U.S. Ser. No. 07/992,640, filed 18 Dec. 1992 now abandoned; which is a continuation of International application no. PCT/US91/03908, filed 7 Jun. 1991; which is a continuation of U.S. Ser. No. 07/545,943, filed 28 Jun. 1990, abandoned.

INTRODUCTION

This invention relates to coated medicaments and a process for providing spray coated gelatinous coverings for such medicaments. This invention is also directed to novel gelatinous compositions for spray coating tablets, caplets, pellets, granules and the like.

BACKGROUND OF THE INVENTION

European Patent Application 88301401.1 (Publication No. 0 279 682, published Jun. 24, 1988), as well as European Patent Application 88311447.2 (Publication No. 0 319 318, published Jul. 6, 1989) and U.S. Pat. No. 4,820,524, granted 11 Apr. 1989; Ser. No. 16,914, filed 20 Feb. 1987), describes a procedure for coating solid cores, such as caplets, with gelatinous coatings to produce a shiny, capsule-like medicament by individually dipping and drying first one end, and then the other end of each caplet to provide a gelatinous coating. In addition, the patent describes in the background section that:

A coating-pan system has a perforated pan or a drum which revolves in a manner similar to a standard clothes dryer. The system includes an air-atomization, spray gun which is inserted into the center of the drum for spraying a fine mist of coating material. A batch of solid medicaments or caplets is typically introduced into the cylindrical pan, wherein said batch is caused to tumble. The tumbling action tends to smooth out some of the rough edges on the caplets prior to coating with organic or aqueous film solutions which may contain solid additives. Coating pans generally produce consistent coating thicknesses and weights but are capable of providing only one color coating. Coatings produced by this method are often thin, offering poor coverage of medicament imperfections and rough edges are not removed by the rambling operation. Unless time is taken to build up a thicker coat, defects on the solid core result in a medicament that does not exhibit a pleasing appearance and may be perceived as being harder to swallow. Moreover, coating abrasion occurring during tumbling produces a surface finish on these medicaments that fails to exhibit the shiny surface that consumers and those in the art have associated with ease of swallowability. Applicant has pan coated caplets with gelatin on an experimental basis and has measured coating thicknesses of only about 6 mils. Moreover, these pan coated gelatin caplets were not observed to be as shinny as caplets coated by a dipping process.

Thus, although the production of pan coated gelatin caplets is disclosed the prior art teaches away from the use of spray coated gelatin coatings. The foregoing publication(s) do not disclose the composition of the gelatin solution(s) utilized for spray application.

Japanese Patent No. 65009992 is directed to a film-coating method using gelatin for coating tablets in equipment used for sugar coating. The water soluble gelatin described in this patent is pre-treated with water in a pressure-cooker at 120°–140° C. for 30–60 minutes to reduce the adhesive properties of the gelatin to allow coating of the tablet. Example 1 of this patent described a formula for film coating comprising water soluble gelatin 1000 g, glycerin 100 g, glycerin monosterate 85 g, Sucrose fatty acid ester 20 g, sweetener, artificial color and distilled water 2500 g.

Japanese Patent No. 6500999 is directed to a film-coating method using gelatin for coating tablets in equipment used for sugar coating with an emulsion including a mixture of hot water, gelatin, a surface active agent and a member selected from fat, paraffin, and wax. The use of the emulsion described in this patent allows tablets to be coated with gelatin in sugar coating equipment where the gelatin emulsion is introduced to cover the surface of the tablets slightly and rotation of the pan and warm air used to dry the tablets.

Japanese Patent No. 60084215 is directed to a film-coating method using gelatin for coating tablets with a composition of coating agent made of film coating base (including gelatin) and brulan.

Japanese Patent No. J74011044B (Derwent 74-27941V/15) is directed toward a coating for medicinal compositions containing a suspension of powdery gelatin in an organic solvent.

British Specification 930,422 (Derwent 66-08131f) is directed to a process for the encapsulation of particles of material by a liquid-liquid phase separation process and in particular to such a process in which the encapsulated particles are spray dried. Examples of suitable gelable hydrophilic colloid materials included gelatin.

SUMMARY OF THE INVENTION

The invention relates to a novel method for spray coating solid pharmaceutical medicaments, namely tablets, caplets, pellets, granules and the like with a gelatinous coating.

The gelation solution utilized consists essentially of gelatin, a plastizier, a surface active agent, water and optionally a coloring agent.

DETAILED DESCRIPTION OF THE INVENTION

The present invention provides a novel method for spray coating tablets, caplets, pellets, granules and the like with a gelatinous coating. The subject invention may be performed with conventional-pan coating systems, preferably a side-vented coating pan such as the Accela-Cota coating pan (24"), with an air atomization spray gun which is inserted into the center of the pan for spraying a fine mist of gelatin solution at an inlet temperature of less than 40° C. (preferably about 25° C.) and an outlet temperature of 20° C or less (preferably less than 20° C.).

A preferred spray apparatus is the Binks Model 610 Air Gun, 66 Fluid Nozzle and 66 PE Air Cap with a Cole parmer master flex pump (7015 pump head) and a delivery rate of 5–50 gm/7 kg batch per minute per gun (2 guns/pan).

The preferred gelatin solution of the present invention consists essentially of Gelatin NF (Powder, Type B, Bloom 275), a plasticizer (triacetin), polysorbate 80, water and optionally containing a coloring agent to produce opaque or transparent colors such as red, white, pink, green, brown, blue, yellow and black.

Examples of plasticizer's which can be used in the present invention include triacetin (glyceryl triacetate), dibutylsebcate and diethyl phthalate.

Examples of surface active agents which can be used in the present invention include polysorbate 80, sodium lauryl sulfate, polysorbate 60 and lecithin.

If desired, the gelatin solution can contain a therapeutic agent that can be applied to an inert core or a core that contains the same or different therapeutic agent.

The gelatin solutions of the present invention contain less than 35% w/w gelatin (preferably 15–25%, more preferably about 20%), 2–20% w/w plasticizer (preferably 2–10% triacetin, more preferably about 6%), 0.5–10% w/w surface active agent (preferably 1–5% polysorbate 80, more preferably about 1%) and water.

If desired, any absorption of the gelatinous coating or the moisture in the gelatinous coating by the solid medicament may be reduce by applying a conventional precoat sealant to the solid prior to spraying the gelatinous solution. See Baker, U.S. Pat. No. 3,185,626, which is herein incorporated by reference. Without a precoat sealant, it is possible that some of the gelatinous coating or moisture in the coating may seep into the solid, resulting in a duller surface. The gelatinous coating of this invention are generally provided in substantially uniform thickness of about 2 to 10 mils, preferably about 3 to 7 mils. However, it may be understood by those familiar with spray coating processes that the coating thickness may be varied to provide a smoother, easier to swallow, medicament.

In order that the invention may be more fully understood it will now be described in more detail, though only by way of illustration, with reference to the following examples.

EXAMPLE 1

Preparation of Gelatin Solution

| | |
|---|---|
| Gelatin Powder (Type B, Bloom 275) | 200 Gm |
| Triacetin | 60 Gm |
| Polysorbate 80 | 10 Gm |
| Yellow #5 (optional) | 0.2 Gm |
| Water qs ad | 1000 Gm |

The water is preheated to 75° C. and the gelatin added into the water with agitation. While maintaining the temperature above 65° C., the triacetin and polysorbate 80 is added with agitation.

The gelatin solution is maintained at a temperature above 70° C. and applied to tablets by spray coating the solution from above onto the tumbling tablets according to the following parameters and equipment set up.

Pan: Accela-cota 24"

Spray apparatus: Binks Model 610 Air Gun, 66 Fluid Nozzle, 66 PE Air Cap

Air Atomization: 30 psi

Deliver System: Cole parmer Master flex pump, 7015 Pump head

Deliver rate: 5–50 Gm/7 kg batch per minute per gun

Exhaust air: 300 cfm

Inlet temperature: 25° C.

Outlet temperature: less than 200° C.

After applying the gelatinous coating to the desired thickness, the pan is rotated with air drying until the tablets are dried without tackiness.

Following the general procedure of Example 1, pellets or granules can also be spray coated in the same manner.

EXAMPLE 2

Coating of Placebo Caplet Cores

PART A: 500 mg. Tablet Core:

The formulation of this example contains the materials shown below:

| | |
|---|---|
| Avicel PH 102 | 30 Kg |
| Magnesium stearate | 150 Gm |

Mix ten minutes and compress on a Manesty Beta press using caplet shaped tooling 0.75 inches×0.25 inches with 1×5 tonnage at a speed of 1000 caplets per minute.

PART B:

| | |
|---|---|
| Caplet core (Part A) | 8 Kg |
| Gelatin Powder | 640 Gm |
| Triacetin | 192 Gm |
| Yellow #5 Dye | 0.7 Gm |
| Red #40 | 0.1 Gm |
| Tween 80 | 32 Gm |
| Distilled Water | 3.2 Kg |

Dissolve the Triacetin (Glyceryl Triacetate), Dye(s), Tween 80 into the water. Heat the resulting solution to 70° C. and add the gelatin to the solution. The gelatin solution is maintained at 70° C. and sprayed unto the caplets according to the following parameters (Spray rate: 20–30 Gm/min; Air Atomization 35 lb/in$^2$; Inlet Air 25° C.; Outlet Air 18°–20° C.) using the equipment of Example 1 to produce a film of 10 mil. (mm) in thickness and showing gold shinny finish.

EXAMPLE 3

Coating of Ibuprofen Caplet Cores

PART A: 309 mg. Tablet Core:

The formulation of this example contains the materials shown below:

| | |
|---|---|
| Corn Starch NF | 26.7 Gm |
| Ibuprofen USP | 646 Gm |
| Colloidal Silicon Dioxide NF | 3.23 Gm |
| Pregelatinized Starch NF | 35.6 Gm |
| Purified Water USP | 280 ml |

To a high speed granulator, add the dry ingredients and mix for one minute. To the premix of dry materials and the water, and mix for two minutes. Discharge the batch, dry and pass through a Comil. Add Stearic Acid NF (5.65 Gm.), Colloidal Silicon Dioxide NF (1.9 Gm) and Corn Starch (40.4 Gm) and mix for ten minutes and compress on a Manesty Beta press using caplet shaped tooling (⅝" inches× ¼" inches) to make cores containing 200 mg Ibuprofen/ Caplet.

PART B:

| | |
|---|---|
| Caplet core (Part A) | 8 Kg |
| Gelatin Powder | 640 Gm |
| Triacetin | 192 Gm |
| Yellow #5 Dye | 0.7 Gm |
| Red #40 | 0.1 Gm |
| Tween 80 | 32 Gm |
| Distilled Water | 3.2 Kg |

Dissolve the Triacetin (Glyceryl Triacetate), Dye(s), Tween 80 into the water. Heat the resulting solution to 70° C. and add the gelatin to the solution. The gelatin solution is maintained at 70° C. and sprayed unto the caplets according to the following parameters (Spray rate: 20–30 Gm/min; Air Atomization 35 lb/in$^2$; Inlet Air 25° C.; Outlet Air 18°–200° C.) using the equipment of Example 1 to produce a film of desired in thickness and showing gold shinny finish.

We claim:

1. The method of spray coating solid pharmaceutical medicaments which comprises tumbling said medicament in a rotating coating pan apparatus and applying to the surface of said medicament, by an air atomization spray gun at an inlet temperature of less than 40° C. and outlet temperature of 20° C. or less, a gelatin solution consisting essentially of less than 35% w/w gelatin, 2–20% w/w triacetin, 0.5–10% w/w surface active agent, water and optionally a coloring agent.

2. The method according to claim 1, in which the gelatin solution contains 15–25% w/w of gelatin and 2–10% w/w triacetin.

3. The method according to claim 2, in which the surface active agent is polysorbate 80.

4. The method according to claim 3, in which the percentage by weight of the polysorbate 80 in the gelatin solution is from about 1% to about 5% w/w.

5. The method according to claim 4, in which the gelating solution contains about 20% w/w gelatin and about 6% w/w triacetin.

6. The method according to claim 5, in which the outlet temperature is less than 20° C.

7. The method of spray coating tablet or caplet cores which comprises tumbling said cores in a rotating coating pan apparatus and applying to the surface of said cores, by an air atomization spray gun at an inlet temperature of less than 40° C. and outlet temperature of 20° C. or less, a gelatin solution consisting essentially of less than 35% w/w gelatin, 2–20% w/w triacetin, 0.5–10% w/w surface active agent, water and optionally a coloring agent.

8. The method according to claim 7, in which the gelatin solution contains 15–25% w/w of gelatin and 2–10% w/w triacetin.

9. The method according to claim 8, in which the surface active agent is polysorbate 80.

10. The method according to claim 9, in which the percentage by weight of the polysorbate 80 in the gelatin solution is from about 1% to about 5% w/w.

11. The method according to claim 10, in which the gelatin solution contains about 20% w/w gelatin and about 6% w/w triacetin.

12. The method according to claim 11, in which the outlet temperature is less than 20° C.

13. The method according to claim 12, in which the percentage by weight of the polysorbate 80 in the gelatin solution is from about 1%.

14. A gelatinous composition adapted for spraying coating tablets, caplets, pellets or granules consisting essentially of less than 35% w/w gelatin, 2–20% w/w triacetin, 0.5–10% w/w surface active agent, water and optionally a coloring agent.

15. The composition according to claim 14, in which the gelatin solution contains 15–25% w/w of gelatin and 2–10% w/w triacetin.

16. The composition according to claim 15, in which the surface active agent is polysorbate 80.

17. The composition according to claim 16, in which the percentage by weight of the polysorbate 80 in the gelatin solution is from about 1% to about 5% w/w.

18. The composition according to claim 17, in which the gelating solution contains about w/w gelatin and about 6% w/w triacetin.

* * * * *